United States Patent [19]
Szász et al.

[11] 4,306,796
[45] Dec. 22, 1981

[54] SHUTTER ASSEMBLY FOR PHOTOGRAPHING DEVICES WITH PRECISION TIMING FACILITY

[75] Inventors: Károly Szász; Sándor Mészáros, both of Budapest, Hungary

[73] Assignee: Medicor Muvek, Budapest, Hungary

[21] Appl. No.: 175,437

[22] Filed: Aug. 6, 1980

[30] Foreign Application Priority Data

Aug. 7, 1979 [HU] Hungary ............................. ME 2289

[51] Int. Cl.³ .......................... G03B 9/08; G03B 9/20
[52] U.S. Cl. ..................................... 354/233; 354/262
[58] Field of Search ................. 354/233, 226, 261–265

[56] References Cited

U.S. PATENT DOCUMENTS

| | | | |
|---|---|---|---|
| 689,982 | 12/1901 | Morgan | 354/264 |
| 778,334 | 12/1904 | Ricketts | 354/262 |
| 1,716,512 | 6/1929 | Baversfeld et al. | 354/262 |
| 1,883,998 | 10/1932 | Lessler | 354/264 |

FOREIGN PATENT DOCUMENTS

35100  4/1886  Fed. Rep. of Germany ...... 354/264

*Primary Examiner*—Donald A. Griffin
*Attorney, Agent, or Firm*—Haseltine and Lake

[57] ABSTRACT

A between-lens shutter assembly for photographing devices comprising at least two, preferably three rotary plates with axes parallel to the axis of the lenses. Each plate comprises an opening. When the plates are rotated with common speed, the openings move from evenly distributed directions towards the inside opening of the lenses, completely uncover it, then in continued movement close the inside opening again. This way identical opening and closing characteristics and times are provided.

In a method using the shutter assembly exposures are taken from television pictures, in which the length of the exposure period is adjusted to be equal to the period of a television picture and the duration of either an opening or closing section, whereby uniform illumination is ensured for the exposure.

The invention can be used mainly for the precise photographing of X-ray pictures displayed on the screen of a television monitor.

3 Claims, 4 Drawing Figures

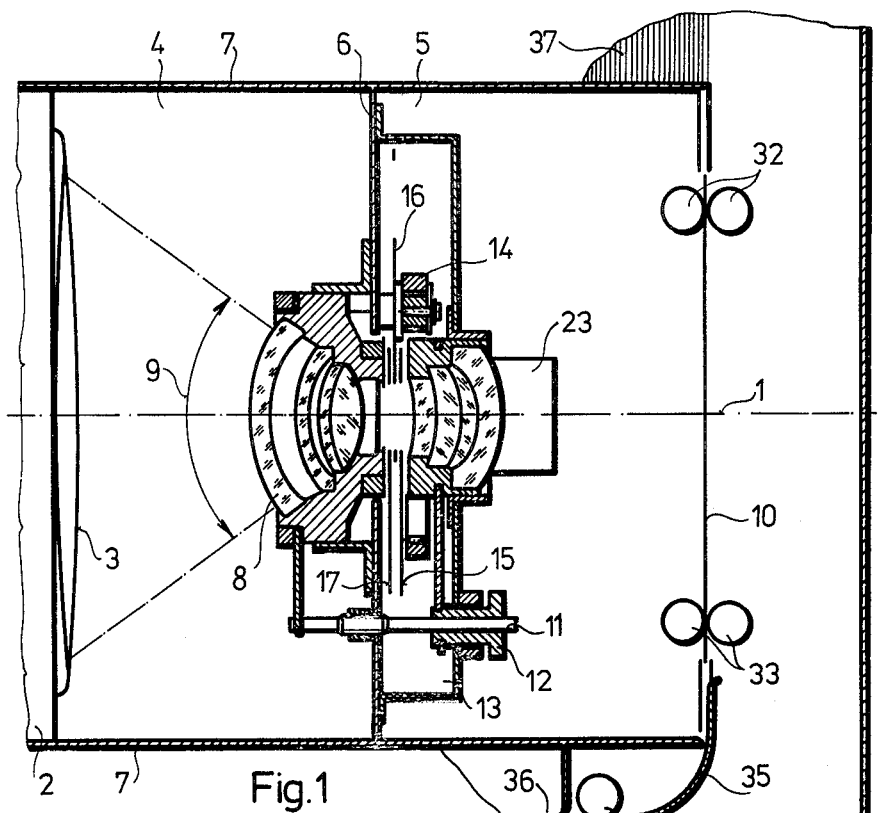
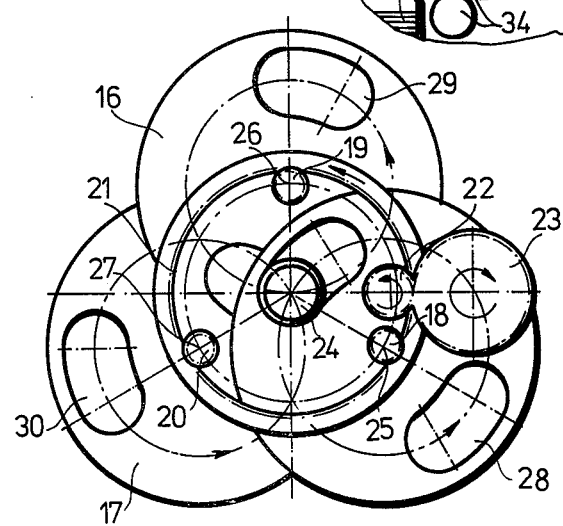

SHUTTER ASSEMBLY FOR PHOTOGRAPHING DEVICES WITH PRECISION TIMING FACILITY

The invention relates to a shutter assembly for photographing devices which has a precision timing facility and which is arranged between two sets of lenses of the optics of the photographing device, the first set is at the object side, while the second set is at the image side of the optics, and the assembly surrounds the inside opening of the optics. The shutter assembly according to the invention is intended at the first place for enabling the precision photographing of a picture displayed on the screen of a television monitor, and as such it is particularly useful for taking roentgenograms from a monitor screen.

In professional photographing technique the way and characteristic of the opening and closure of the optics carried out by a shutter assembly has a significant role. The more perfect the shutter construction is, the shorter the opening and closure period are compared to the fully open condition. The opening and closure characteristics of the optics have in the first place a decisive role, when exposures should be taken from a television screen. As it is known, the picture on the television screen is displayed by means of an electron beam deflected according to a standard raster. This way the complete picture information is never available in any moment on the screen.

During the opening and closure process only a part of the light intensity of the screen will fall on the light-sensitive film, and the blackening of the corresponding film areas will be other than the blackening of the areas exposed when the optics is completely open. When roentgenograms should be taken from a monitor screen, owing to the possibility of an accidental movement of the patient or of the displacement of an examined phenomenon within the body of the patient, the duration of an exposure cannot last more than about the duration of a complete television picture, which is 40 msec. when the mains frequency is 50 Hz. In order that the light sensitive film should receive picture information coming from one end and the same picture, the opening condition of the optics should last exactly the duration of a picture, because in areas where the film receives picture information coming from more than one picture, the contrast will change.

With the above requirements the characteristic of the opening of the optics is also important. The application of conventional, linearly moving slit shutters is not allowed because in that case the opening of the optics occurs unevenly (corresponding to the linearly moving shutter). The evenness of the characteristics of conventional segmented laminar shutters, that annularly close and open the optics can be sufficient, however, at such shutters the opening and closure periods cannot be adjusted to the same values and the characteristic varies during use. In many constructions the opening and closure periods are too long compared to the fully open period of the optics.

Due to the above sketched problems the sufficiently precise photographing of a television picture has been solved so far.

The task of taking precise exposures will be more complicated by the fact that the illuminated condition of the television screen occurs not only in the areas where the electron beam momentarily falls, but the light intensity of the previously illuminated areas is maintained for a while and it is decreasing according to the illumination characteristics of the phosphorous layer of the screen. The precise photographing should be solved in such a way, that the evenness of the contrast should be maintained in spite of the remembering behaviour of the screen.

In case of X-ray photographing technique the illumination of the film should be determined by the picture information only, because the inhomogenities of the illumination coming from the imperfect way of a photographic exposure might disturb the work of picture evaluation for the X-ray specialist.

The object of the invention is to provide a shutter assembly with precision timing facilities, in which the length and characteristic both in the opening and closing sections are identical, in which the opening and closing of the optics take place from a number of directions simultaneously, and which provides for the precision photographing of a television screen.

According to the invention a shutter assembly with precision timing facility has been provided for photographing devices that comprise an optics with respective sets of lenses at the object side and at the image side thereof and the optics defines an inside opening for passage of light beams therethrough, and the shutter assembly is arranged between the two sets of lenses and it encircles the inside opening of the optics. The shutter assembly is characterized by at least two rotary plates adapted for rotational movement with identical speed, in which the axes of the rotary plates extend in parallel with the optical axis of the optics, but these axes are offset from the optical axis in radical direction with a distance greater than the radius of the inside opening of the optics, and the rotary plates cover the inside opening and define respective openings with radial width which is at least equal with the size (diameter) of the inside opening. When the rotary plates are rotated, the openings will reach positions in which they completely uncover the inside opening.

The term "inside opening" defines the cross section of the optics through which light can pass between the two sets of lenses.

In a preferable embodiment the axis of each rotary plate is at the same distance from the optical axis, and these axes fall in the apex points of a hypotetical regular polygon that has just as much apex points as the number of the rotary plates is, when viewed in a plane normal to the optical axis.

In a further preferable embodiment all openings defined in the rotary plates have identical shape, and corresponding points on these openings fall in the apex points of a hypotetical regular polygon when viewed in a plane normal to the optical axis. The order of the polygon corresponds to the number of the rotary plates.

Due to the arrangement of the rotary plates and the openings defined therein according to the apex points of a regular polygon, it was ensured that the openings move from evenly distributed direction towards the inside opening of the optics, whereby the opening and closing process of the optics will occur according to preferable geometric paths.

The identical shape of the openings forms one of the conditions for the identical opening and closing durations and characteristics.

It is preferable, if the axes of the rotary plates are coupled with respective cog-wheels with identical tooth number that engage a common annular gear with inside or outside gearing, whereby the rotational speed of the rotary plates will be identical.

According to the invention a method has also been provided for taking photographic exposures from television pictures, in which the above described shutter assembly is used, and during the method the rotary plates are turned with common angular speed, and the inside opening of the optics is opened through a period defined between the starting moment and the finishing moment of the opening process, and the duration of this period is adjusted to be the combined duration of a complete television picture and either of the duration of the opening or closing sections.

When an exposure is taken according to this method, during the opening and closing sections identical picture details will be illuminated in such a way that the combined effect of the double illumination will be identical to the illumination that occurs with completely open optics.

With shutter assemblies designed according to the invention in case of an opening period of 40 msec. (that corresponds to a picture period) the duration of the opening and closing sections was adjusted to a preferable value of 0.8 msec. which value remained always the same in each exposure. The invention will now be described in connection with preferable embodiments thereof, in which reference will be made to the accompanying drawings. In the drawings FIG. 1 shows a photographing device equipped with the shutter assembly according to the invention in schematical elevational sectional view;

FIG. 2 shows the side view of the shutter assembly shown in FIG. 1;

Figure 4:
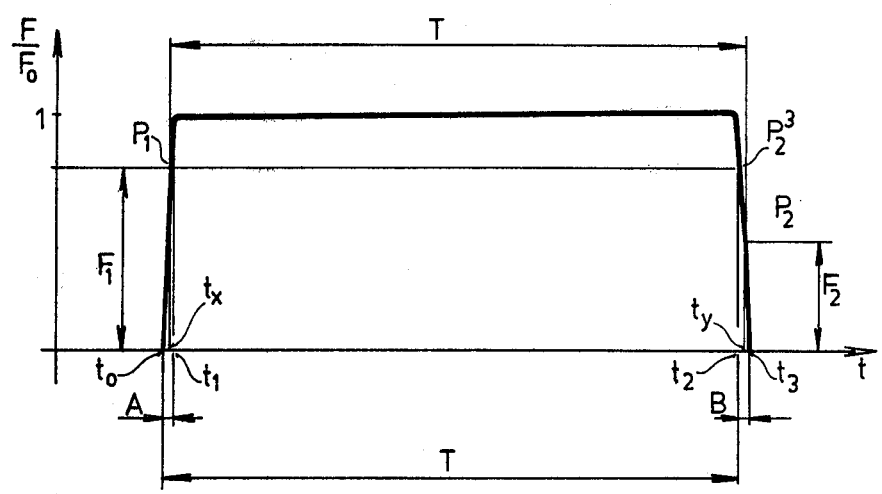
FIG. 4 is the time diagram of the relative light-flux passing through the inside opening of the optics.

The apparatus shown in FIG. 1, which is adapted for taking photographs from a television picture displayed on a monitor screen, comprises an optical axis 1 defined by the centre of the picture on television monitor 2. The television monitor 2 is surrounded by casing 7, and in the end region of the casing 7 opposite to the monitor an image plane is defined in which film 10 is arranged. The interior of the casing is divided in two parts by wall 6 i.e. in part 4 which falls to the objective side of the wall 6 that faces to screen 3 of the television monitor, and in part 5 on the other side of the wall 6 facing towards the image plane with the film 10. The casing 7 and the wall 6 mounted thereto form part of the constructional support of the apparatus. A multi-lens optics 8 is fixed in the wall 6 comprising lenses both in the objective and image sides of the walls. A shutter assembly 14 is arranged between the two sets of lenses in room 13, the construction of which will be explained later. The shutter assembly 14 is arranged around inside opening 24 of the optics 8 (FIG. 2).

The geometrical sizes of the apparatus is defined by the focal distance and the angular width 9 of the optics 8 which are designed in accordance with the required image size imaged on the film 10 in the image plane. The focal distance of the optics 8 can be adjusted by changing the axial position of the two sets of lenses by means of focus adjusting elements 11 and 12. In the exemplary embodiment shown in FIG. 1 the focus adjusting elements 11 and 12 are formed by respective threaded bolts and nuts. The axial position of the set of lenses in the image side is fixed, and the set of lenses in the objective side is mounted to the wall in such a way that allows its axially guided displacement. By changing the focal distance the picture on the screen 3 can be adjusted to be sharply imaged in the image plane.

In an alternative embodiment (not shown in the drawing) the image adjustment can be carried out with fixed relative arrangement of the two sets of lenses of the optics 8 and the shutter assembly 14 located therebetween by changing the axial position of the wall 6. In that case the wall 6 should be connected to the casing 7 in a way that allows its axially guided displacement.

It should be provided for that during the photographic exposure of the viewing screen 3 exactly one and only one complete television picture can mark a trace in the film 10. For that purpose the design of the shutter assembly 14 should see to this condition by providing specific opening and closure characteristics.

The structural design of the shutter assembly 14 is illustrated in FIG. 1 schematically only, but it can be seen that it comprises three rotary plates 15, 16 and 17 located in respective planes normal to the optical axis 1 in such a way that the middle rotary plate 16 can be turned between the two neighbouring outer rotary plates 15 and 17.

FIG. 2 shows the shutter assembly 14 in a schematical illustration. Of the axes of the three rotary plates 15, 16 and 17 only the three respective fulcrums 25, 26 and 27 can be seen in FIG. 2 which are arranged in the apex points of an imaginary regular triangle. Respective cogwheels 18, 19 and 20 are mounted on the three axes that engage an annular gear 21 with internal gearing having sufficiently great inner diameter. The annular gear 12 is driven by step motor 23 through intermediate gear 22. In FIG. 2 respective arrows show the sense of rotation of each wheel.

Each of the rotary plates 15, 16 and 17 comprises a pair of openings 28, 29, and 30 and the radial width of the openings is at least equal to the diameter of the inside opening 24 of the optics 8.

If any arbitrarily selected point of each of the openings 28, 29 and 30 is connected through respective imaginary straight lines with the optical axis 1, then these straight lines that cross each other in the axis 1 will always close angles of 120°. It can be understood that when the step motor 23 is running, the openings 28, 29 and 30 will periodically move towards and away from the optical axis 1. When moving towards the axis 1, the inside opening 24 will be uncovered, then it will be covered again when the openings move away from the axis. While in the exemplary embodiment each of the rotary plates 15, 16 and 17 comprise a pair of openings, in each complete revolution of the rotary plates the inside opening 24 will be twice completely uncovered and covered again.

In the exemplary embodiment the front and rear ends of the openings 28, 29 and 30 are defined by circular arc sections having centres falling on an imaginary annular path of each rotary plate 15, 16 and 17 that crosses the optical axis 1. It can be appreciated that other shapes can also be used for the end sections of the openings 28, 29 and 30, any shape, however, should meet the condition that the front and rear end sections of any opening should have corresponding shapes, whereby the opening and closure processes of the inside opening 24 will have identical characteristics.

The angular width (length of the arc) of the openings 28, 29 and 30 defined between their respective end sections determines substantially the length of the open period of the shutter assembly 14, which open period is also dependent on the speed of the step motor 23 that defines directly the speed of revolution of the rotary plates 15, 16 and 17.

Referring now again to FIG. 1 the way of movement of the film 10 arranged in the image plane will be described. The film 10 is moved from a storage place 37 through pairs of rollers 32, 33 and 34 to collecting station 36. A guiding arc plate 35 is used for diverting the film into the required direction. The film transport mechanism is arranged in room 31 which is inside the housing of the apparatus and it is protected from the penetration of outer light.

Figure 3:
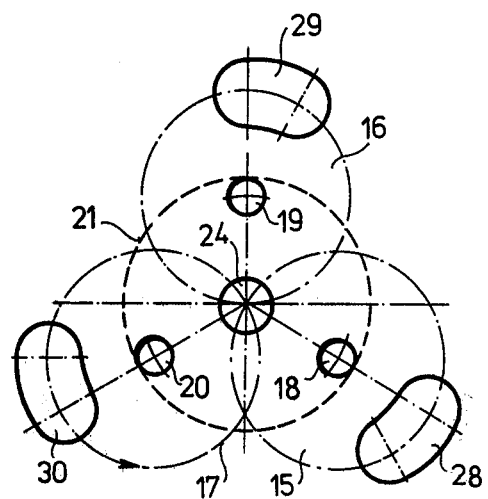
FIG. 3 is a simplified schematic illustration for the operation of the shutter assembly.

FIG. 3 is a kinematic illustration for the operation of the shutter assembly. In this figure only the openings 28, 29 and 30 of the three rotary plates 15, 16 and 17 are shown together with the driving cog-wheels 18, 19 and 20 for the rotary plate. For case of simplicity each rotary plates was supposed to comprise a single opening only.

The operation of the shutter assembly is as follows. It is supposed that at the beginning of an exposure all the three openings are in the starting position as shown in FIG. 3, and the inside opening 24 is closed by the rotary plates 15, 16 and 17. When the assembly is started to move, the annular gear 21 rotates with uniform angular speed, whereby the openings 28, 29 and 30 will approach towards the inside opening 24 along respective circular paths as shown by the arrows in FIG. 3. When the openings 28, 29 and 30 reach from three directions the inside opening 24, the light path through the inside opening 24 will be quickly uncovered. The light can pass through the inside opening 24 as long as the openings 28, 29 and 30 enable it. The rotation of the rotary plates 15, 16 and 17 goes on, and their openings 28, 29 and 30 will move away from the inside opening 24 with the same speed and on corresponding paths as they have approached to it. The rotation of the rotary plates 15, 16 and 17 lasts till they move again in the starting position shown in FIG. 3.

FIG. 4 shows the time diagram of the relative light flux $F/F_o$ streaming through the inside opening 24.

In the FIG. 4 in the moment $t_o$ the front edges of the openings 28, 29 and 30 just reach the outer side of the inside opening 24 during their approach thereto. Thereafter the light flux through the inside opening rapidly increases according to a characteristics corresponding to the shape of the openings 28, 29 and 30, and in the moment $t_1$ the full cross-section of the inside opening 24 will be free, and the value of the relative light flux $F/F_o$ will be unity. This condition lasts till the moment $t_2$ when the rear edges of the openings 28, 29 and 30 reach the outer side of the inside opening 24. From now on the openings move away from the inside opening 24 and the relative light-flux rapidly decreases. In the moment $t_3$ the rotary plates completely close the inside opening 24.

In the above sketched construction the light flux varies both in opening section A and closing section B according to identical characteristics.

In connection with FIG. 4 the conditions required for the photographing of a complete television picture will be examined, if the exposure should provide a uniform and undistorted illumination. It will be supposed that the picture frequency is 25 Hz and the corresponding duration T of each picture is T=40 msec. It will also be supposed that between the moments $t_o$ and $t_2$ just T=40 msec. time has elapsed. This means that the electron beam that forms the picture on the screen falls on the same point of the screen 3 in the moments $t_o$ and $t_2$.

It can be seen that in the opening section A, which lasts through 0.8 msec., the illumination will be smaller than between the moments $t_1$ and $t_2$ when full illumination is ensured. This means that a band on the picture beginning at the starting position of the electron beam in the moment $t_o$ and having a predetermined width corresponding to the length of the opening section A will have a gradually increased illumination. In order to ensure a uniform illumination for the picture, the required missing illumination should be added in the closing section B. In point $P_1$ that falls about the middle of the opening section A, the relative light flux has a value $F_1$. A complete period T following the moment $t_x$ of the point $P_1$, i.e. in the moment $t_y = t_x + T$ the electron beam illuminates the same part of the screen as in point $P_1$. In the diagram of FIG. 4 the curve is at point $P_2$ in the moment $t_y$. As it was explained, the points $P_1$ and $P_2$ are associated with one and the same location on the screen. It can be seen in FIG. 4 that in the moment $t_y$ the relative light flux has a value $F_2$. Owing to the fact that the opening and closing sections A and B have identical characteristics with inverted sense, it can be understood that the sum of the relative light fluxes $F_1$ and $F_2$ corresponding to the points $P_1$ and $P_2$ that define the same location on the screen will be unity, i.e. $F_1 + F_2 = 1$. Since the duration of the opening and closing sections A and B is identical, it will be obvious on the basis of the same train of thoughts that every location on the screen, which was associated in the opening section A with an illumination smaller than unity, will be associated in the closing section B with the complementary illumination required to reach the unity value, whereby the illumination of the complete picture will be uniformly unity, if the above conditions are met.

In the closing section B the picture information of the next picture is used, this information, however, due to the very small time difference between two subsequent pictures can be considered to be substantially identical with the information of the previous picture. The exact adjustment of the period time T can be carried out by finely changing the speed of the rotary plates 15, 16 and 17.

In the embodiments shown in FIGS. 1, 2 and 3 the shutter assembly comprised three rotary plates. Obviously, by using the same principle, if the number of the rotary plates is increased, more favourable opening and closing characteristics can be attained. The increased number of the rotary plates, however, makes the constructional design more complicated, and according to our experiences the application of more than three rotary plates does not provide substantially better results. In an extreme case the number of the rotary plates can be reduced to two, but in that case the opening and closing characteristics will be quite noticably less favourable than in case of using three rotary plates.

We claim:

1. A method for making a photographic exposure from a television picture by using a shutter assembly 14 comprising at least two rotary plates (15, 16, 17) adapted for rotary movement with identical speed around respective axes extending parallel to an optical axis (1) of optics (8) and being radially offset therefrom, said rotary plates (15, 16, 17) being arranged to completely cover an inside opening (24) and define respective openings (28, 29, 30) having a radial width being at least equal to the size of said inside opening (24), during rotational movement of said rotary plates said openings (28, 29, 30) move in positions in which said inside opening (24) is completely uncovered by said rotary plates, comprising the steps of: rotating said rotary plates with uniform angular speed and uncovering said inside opening (24) of said optics (8) for a period defined between a starting moment ($t_o$) and a finishing moment ($t_3$), said uncovering period comprises an opening section (A) with partly open inside opening, an open period with completely open inside opening and a closing section (B) with partly open inside opening, and adjusting the duration of said uncovering period to be the combined length of a full picture duration (T) of the television picture and either of the duration of said opening or closing sections (A or B).

2. A shutter assembly for photographing devices with precision timing facility, in which said photographic device comprises an optics defining an inside opening consisting of a set of lenses at its object side and a further set of lenses at its image side, said shutter assembly being arranged between said sets of lenses and surrounding said inside opening, characterized in that said shutter assembly (14) comprises at least two rotary plates (15, 16, 17) adapted for rotary movements with identical speed around respective axes extending parallel to the optical axis (1) of said optics (8) and being radially offset therefrom with a distance at least equal to the radius of said inside opening (24), said rotary plates (15, 16, 17) being arranged to completely cover said inside opening (24) and define respective openings (28, 29, 30) having radial width being at least equal to the size of said inside opening (24), and during rotational movements of said rotary plates said openings (28, 29, 30) being moved in positions in which said inside opening (24) gets completely uncovered by said rotary plates, said rotary plates (15, 16, 17) having axes being arranged in identical radial distances from said optical axis (1), and said axes falling in the apex points of an imaginary regular polygon of the order corresponding to the number of said rotary plates (15, 16, 17) when viewed in a plane normal to said optical axis (1), said rotary plates (15, 16, 17) define said openings (28, 29, 30) with identical shapes, and corresponding points of said openings (28, 29, 30) fall in said normal plane in the apex points of a regular polygon with the same order as said polygon and respective cog-wheels (18, 19, 20) being coupled to the axes of said rotary plates (15, 16, 17) and having identical tooth number, and an annular gear (21) coupled to all of said cog-wheels (18, 19, 20).

3. The shutter assembly as claimed in claim 2, comprising an intermediate gear (22) coupled to said annular gear (21) and a step motor (23) coupled to and driving said intermediate gear (22).

* * * * *